US00PP24940P2

(12) United States Plant Patent
van de Meer

(10) Patent No.: US PP24,940 P2
(45) Date of Patent: Sep. 30, 2014

(54) ***ASTILBE* PLANT NAMED 'CAPPUCCINO'**

(50) Latin Name: ***Astilbe japonica*×*Astilbe arendsii***
Varietal Denomination: Cappuccino

(71) Applicant: Hans van de Meer, Nieuwe Wetering (NL)

(72) Inventor: Hans van de Meer, Nieuwe Wetering (NL)

(73) Assignee: Compass Plants B.V., Hillegom (NL)

( * ) Notice: Subject to any disclaimer, the term of this patent is extended or adjusted under 35 U.S.C. 154(b) by 48 days.

(21) Appl. No.: 13/694,816

(22) Filed: Jan. 7, 2013

(51) Int. Cl.
*A01H 5/00* (2006.01)

(52) U.S. Cl.
USPC ..... Plt./407

(58) Field of Classification Search
USPC ..... Plt./407
See application file for complete search history.

*Primary Examiner* — Kent L Bell
(74) *Attorney, Agent, or Firm* — C. A. Whealy

(57) ABSTRACT

A new and distinct cultivar of *Astilbe* plant named 'Cappuccino', characterized by its compact, broadly upright and mounding plant habit; dark green-colored leaves; freely and uniformly flowering habit; white-colored flowers positioned just above the foliar plane on strong and dark purple-colored peduncles; and good container and garden performance.

3 Drawing Sheets

Botanical designation: *Astilbe japonica*×*Astilbe arendsii*.
Cultivar denomination: 'CAPPUCCINO'.

BACKGROUND OF THE INVENTION

The present invention relates to a new and distinct cultivar of *Astilbe*, botanically known as *Astilbe japonica*×*Astilbe arendsii* and hereinafter referred to by the name 'Cappuccino'.

The new *Astilbe* plant is a product of a planned breeding program conducted by the Inventor in Roelofarendsveen, The Netherlands. The objective of the breeding program was to create new uniform and freely flowering *Astilbe* plants with attractive leaf and flower coloration.

The new *Astilbe* plant originated from a cross-pollination made by the Inventor in 2002 in Roelofarendsveen, The Netherlands, of an unnamed selection of *Astilbe japonica*, not patented, as the female, or seed, parent with an unnamed selection of *Astilbe arendsii*, not patented, as the male, or pollen, parent. The new *Astilbe* plant was discovered and selected by the Inventor as a single flowering plant from within the progeny of the stated cross-pollination in a controlled greenhouse environment in Roelofarendsveen, The Netherlands in 2004.

Asexual reproduction of the new *Astilbe* plant by vegetative divisions in a controlled environment in Nieuwe Wetering, The Netherlands since 2004 has shown that the unique features of this new *Astilbe* plant are stable and reproduced true to type in successive generations.

SUMMARY OF THE INVENTION

Plants of the new *Astilbe* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Cappuccino'.

These characteristics in combination distinguish 'Cappuccino' as a new and distinct *Astilbe* plant:

1. Compact, broadly upright and mounding plant habit.
2. Dark green-colored leaves.
3. Freely and uniformly flowering habit.
4. White-colored flowers positioned just above the foliar plane on strong and dark purple-colored peduncles.
5. Good container and garden performance.

Plants of the new *Astilbe* differ primarily from plants of the parent selections in the following characteristics:

1. Plants of the new *Astilbe* are more compact and shorter than plants of the parent selections.
2. Plants of the new *Astilbe* are more freely flowering than plants of the parent selections.
3. Plants of the new *Astilbe* have darker-colored leaves than plants of the parent selections.
4. Plants of the new *Astilbe* have broader inflorescences than plants of the parent selections.

Plants of the new *Astilbe* can be compared to plants of *Astilbe arendsii* 'Diamant', not patented. In side-by-side comparisons conducted in Hillegom, The Netherlands, plants of the new *Astilbe* and 'Diamant' differed in the following characteristics:

1. Plants of the new *Astilbe* were shorter and more compact than plants of 'Diamant'.
2. Plants of the new *Astilbe* had darker-colored leaves than plants of 'Diamant'.
3. Plants of the new *Astilbe* were more freely flowering than plants of 'Diamant'.
4. Inflorescences of plants of the new *Astilbe* and 'Diamant' differed in peduncle and pedicel color as plants of 'Diamant' had green-colored peduncles and pedicels.
5. Plants of the new *Astilbe* and 'Diamant' differed slightly in flower color as plants of 'Diamant' had creamy white-colored flowers.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of typical flowering plants of 'Cappuccino' grown in an outdoor nursery.

The photograph on the second sheet is a close-up view of a typical developing inflorescence of 'Cappuccino'.

The photograph on the third sheet is a close-up view of fully developed inflorescences of 'Cappuccino'.

DETAILED BOTANICAL DESCRIPTION

The aforementioned photographs and following observations, measurements and values describe plants grown during the late summer in an outdoor nursery in Hillegom, The Netherlands and under cultural practices typical of commercial *Astilbe* production. During the production of the plants, day temperatures ranged from 18° C. to 28° C. and night temperatures ranged from 10° C. to 18° C. Plants were one year old when the photographs and description were taken. In the following description, color references are made to The Royal Horticultural Society Colour Chart, 2007 Edition, except where general terms of ordinary dictionary significance are used.

Botanical classification: *Astilbe japonica*×*Astilbe arendsii* 'Cappuccino'.

Parentage:

- *Female, or seed, parent*.—Unnamed *Astilbe japonica* seedling selection, not patented.
- *Male, or pollen, parent*.—Unnamed *Astilbe arendsii* seedling selection, not patented.

Propagation:

- *Type*.—By divisions.
- *Time to initiate roots*.—About three weeks at temperatures about 20° C.
- *Root description*.—Thick, fleshy; brown and white in color.
- *Rooting habit*.—Freely branching; dense.

Plant description:

- *Plant form and growth habit*.—Herbaceous perennial; compact, broadly upright and mounding plant form with inflorescences held just above the foliar plane; flowering stems and leaves basal; freely flowering with numerous basal branches developing per plant; moderately vigorous growth habit; freely and uniformly flowering habit.
- *Growth rate*.—Moderate; from divisions, about ten months are required to produce fully-grown flowering plants in containers.
- *Plant height* (*soil level to top of foliar plane*).—About 40 cm.
- *Plant height* (*soil level to top of inflorescences*).—About 73 cm.
- *Plant width* (*spread*).—About 63.5 cm.
- *Stem description*.—Length: About 39.5 cm. Diameter: About 4 mm. Strength: Strong, sturdy. Texture: Smooth, glabrous. Color: Close to 187A to 187B.

Foliage description:

- *Arrangement*.—Alternate in basal rosettes; biternately compound; about 25 leaflets per leaf.
- *Leaf length* (*excluding petiole*).—About 20.5 cm.
- *Leaf width*.—About 18.6 cm.
- *Terminal leaflet length*.—About 5.9 cm.
- *Terminal leaflet width*.—About 2.7 cm.
- *Lateral leaflet length*.—About 4.7 cm.
- *Lateral leaflet width*.—About 1.9 cm.
- *Leaf shape*.—Roughly deltoid to broadly ovate in outline.
- *Lateral and terminal leaflet shape*.—Elliptic to narrowly ovate.
- *Lateral and terminal leaflet apex*.—Acute.
- *Lateral and terminal leaflet base*.—Rounded to cuneate.
- *Lateral and terminal leaflet margin*.—Biserrate.
- *Lateral and terminal leaflet texture, upper surface*.—Smooth, glabrous.
- *Lateral and terminal leaflet texture, lower surface*.—Moderately pubescent; slightly rough.
- *Lateral and terminal leaflet venation pattern*.—Pinnate.
- *Lateral and terminal leaflet color*.—Developing leaflets, upper surface: Close to N137B. Developing leaflets, lower surface: Close to 147B. Fully expanded leaflets, upper surface: Between N137A and 147A; venation, close to 144B. Fully expanded leaflets, lower surface: Close to 147B; venation, close to 152D.
- *Leaf petiole length*.—About 16.9 cm.
- *Leaf petiole diameter*.—About 3 mm.
- *Leaflet petiole length*.—About 6 mm.
- *Leaflet petiole width*.—About 1 mm.
- *Leaf and leaflet petiole texture, upper and lower surfaces*.—Smooth, glabrous.
- *Leaf and leaflet petiole color, upper and lower surfaces*.—Close to 176A.

Flower description:

- *Flower type and flowering habit*.—Single rotate flowers arrange on broad terminal panicles; flowers face upright, outwardly or drooping depending on position on the inflorescence; racemes roughly conical in shape; freely and uniformly flowering habit with about 1,500 flowers per inflorescence.
- *Fragrance*.—Moderately strong; sweet, pleasant.
- *Natural flowering season*.—Plants begin flowering about ten months after planting; continuously flowering from early to late summer in The Netherlands.
- *Postproduction longevity*.—Flowers last about ten days on the plant; flowers persistent.
- *Flower buds*.—Height: About 2 mm. Diameter: About 1.5 mm. Shape: Broadly ovoid. Color: Close to 155D.
- *Inflorescence height*.—About 34.6 cm.
- *Inflorescence diameter*.—About 27.3 cm.
- *Flower diameter*.—About 9 mm.
- *Flower depth*.—About 5 mm.
- *Petals*.—Quantity per flower: Typically five in a single whorl. Length: About 5 mm. Lobe width: About 1 mm. Shape: Oblanceolate. Apex: Broadly acute. Margin: Entire. Texture, upper and lower surfaces: Smooth, glabrous. Color: Developing petals, upper and lower surfaces: Close to NN155D. Fully expanded petals, upper and lower surfaces: Close to NN155D.
- *Sepals*.—Quantity per flower: Typically five in a single whorl, fused towards the base; campanulate-shaped calyx. Length: About 2 mm. Width: About 0.75 mm. Shape: Ovate. Apex: Acute. Margin: Entire. Texture, upper and lower surfaces: Smooth, glabrous. Color:

Developing sepals, upper and lower surfaces: Close to 157C. Fully expanded sepals, upper and lower surfaces: Close to 157C.

*Peduncles*.—Length: About 33.8 cm. Diameter: About 2.5 mm. Angle: Erect to about 45° from vertical. Strength: Strong. Texture: Smooth, glabrous. Color: Close to 187A to 187B.

*Pedicels*.—Length: About 1 mm. Diameter: About 0.5 mm. Angle: About 50° from peduncle axis. Strength: Moderately strong. Texture: Smooth, glabrous. Color: Close to 145B.

*Reproductive organs*.—Stamens: Quantity per flower: Typically ten. Filament length: About 3 mm. Filament color: Close to NN155D. Anther shape: Ovate, basifixed. Anther length: About 0.2 mm. Anther color: Close to 158A. Pollen amount: Scarce. Pollen color: Close to N155A. Pistils: Quantity per flower: Typically two. Pistil length: About 1.5 mm. Stigma shape: Club-shaped. Stigma color: Close to 165B. Style length: About 1.3 mm. Style color: Close to NN155A. Ovary color: Close to NN155A.

*Seeds and fruits*.—Seed and fruit development have not been observed on plants of the new *Astilbe*.

Disease & pest resistance: Plants of the new *Astilbe* have not been noted to be resistant to pathogens and pests common to *Astilbe* plants.

Garden performance: Plants of the new *Astilbe* have been observed to have good garden performance and tolerate rain, wind and high temperatures of about 35° C. Plants of the new *Astilbe* have been observed to be hardy to USDA Hardiness Zone 5.

It is claimed:

1. A new and distinct *Astilbe* plant named 'Cappuccino' as illustrated and described.

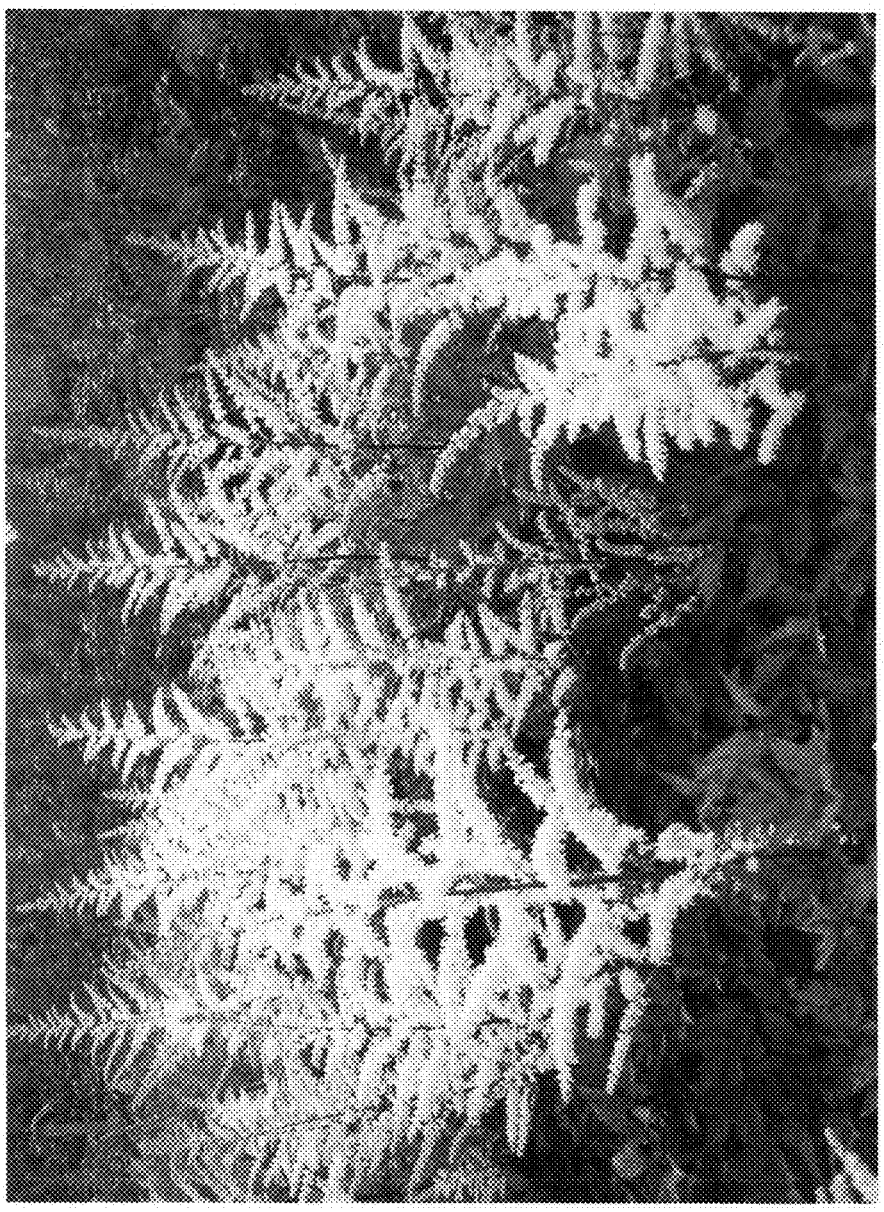

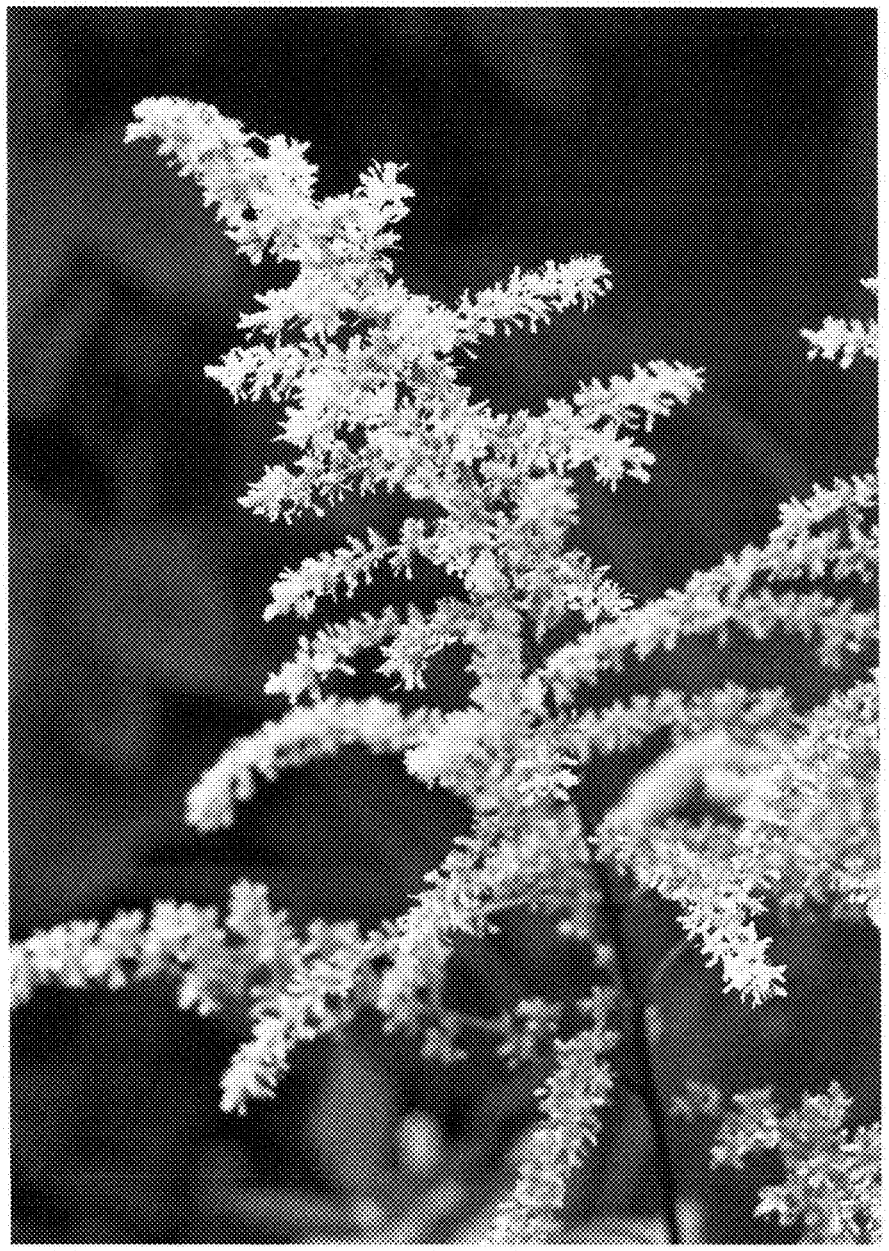

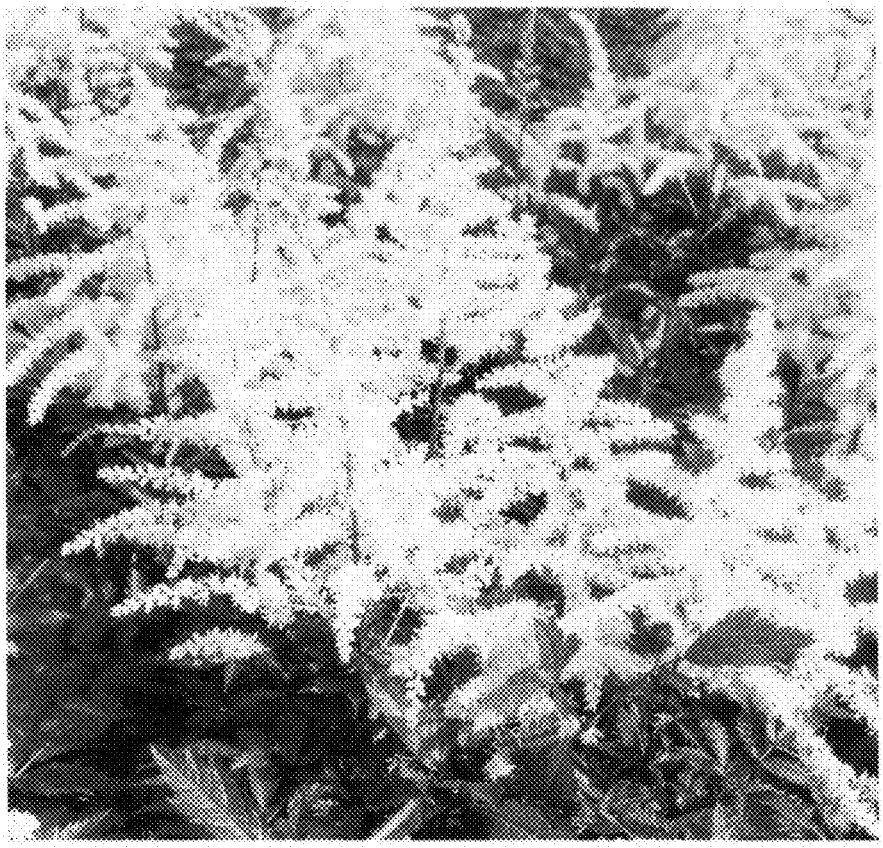

* * * * *